(12) United States Patent
Breindel et al.

(10) Patent No.: US 11,490,840 B2
(45) Date of Patent: Nov. 8, 2022

(54) BLOOD SEQUESTRATION DEVICE AND METHOD

(71) Applicant: Smiths Medical ASD, Inc., Plymouth, MN (US)

(72) Inventors: Jay T. Breindel, Branford, CT (US); Harsh D. Chheda, Cheshire, CT (US)

(73) Assignee: Smiths Medical ASD, Inc., Plymouth, MN (US)

( * ) Notice: Subject to any disclaimer, the term of this patent is extended or adjusted under 35 U.S.C. 154(b) by 445 days.

(21) Appl. No.: 16/451,445

(22) Filed: Jun. 25, 2019

(65) Prior Publication Data
US 2019/0374145 A1 Dec. 12, 2019

Related U.S. Application Data

(63) Continuation of application No. 16/434,284, filed on Jun. 7, 2019.
(Continued)

(51) Int. Cl.
*A61B 5/15* (2006.01)
*A61B 5/153* (2006.01)

(52) U.S. Cl.
CPC .. *A61B 5/150213* (2013.01); *A61B 5/150251* (2013.01); *A61B 5/15003* (2013.01); *A61B 5/153* (2013.01); *A61B 5/150221* (2013.01)

(58) Field of Classification Search
CPC ........ A61B 5/150213; A61B 5/150251; A61B 5/15003; A61B 5/150221; A61B 5/153;
(Continued)

(56) References Cited

U.S. PATENT DOCUMENTS 4,900,311 A * 2/1990 Stern .................... A61M 5/3271
604/198
9,545,495 B2 1/2017 Goral et al.
(Continued)

FOREIGN PATENT DOCUMENTS

WO WO 2011/162772 A1 12/2011
WO WO2018227191 12/2018
WO WO 2019/079719 A1 4/2019

OTHER PUBLICATIONS

Search Report dated Dec. 17, 2019 for Application No. PCT/US2019/035978, 16 pages.
(Continued)

*Primary Examiner* — Sean P Dougherty
*Assistant Examiner* — Alexander H Connor
(74) *Attorney, Agent, or Firm* — Patterson Thuente Pedersen, P.A.

(57) ABSTRACT

A blood sequestration device configured to isolate an initial, potentially contaminated portion of blood from the flow of blood of a patient, prior to directing the flow of blood to an outlet port where the blood can be accessed. The blood sequestration device including a body member having an interior wall defining a fluid conduit having a distal portion, a first proximal portion, and a second proximal portion, wherein the first proximal portion defines a sequestration chamber configured to isolate an initial portion of blood of a flow of blood, a vent path configured to enable the escape of gas initially trapped within the sequestration chamber.

5 Claims, 12 Drawing Sheets

Related U.S. Application Data

(60) Provisional application No. 62/682,362, filed on Jun. 8, 2018.

(58) Field of Classification Search
CPC .......... A61B 5/15074; A61B 5/150389; A61B 5/150908; A61B 5/150992
See application file for complete search history.

(56) References Cited

U.S. PATENT DOCUMENTS

| | | | |
|---|---|---|---|
| D808,013 S | 1/2018 | Chheda et al. | |
| 10,028,691 B2 | 7/2018 | Goral et al. | |
| D844,774 S | 4/2019 | Akcay et al. | |
| D893,711 S | 8/2020 | Chheda et al. | |
| 2004/0068202 A1 | 4/2004 | Hansson et al. | |
| 2004/0143195 A1* | 7/2004 | Bressler ............ | A61M 25/0637 600/573 |
| 2006/0271001 A1* | 11/2006 | Hirota ............... | A61M 25/0637 604/263 |
| 2009/0227953 A1 | 9/2009 | Tan et al. | |
| 2016/0220762 A1 | 8/2016 | Goral et al. | |
| 2016/0220791 A1 | 8/2016 | Akcay et al. | |
| 2017/0020428 A1* | 1/2017 | Rogers ............. | A61B 5/150572 |
| 2017/0239443 A1 | 8/2017 | Abitabilo et al. | |
| 2018/0296149 A1 | 10/2018 | Goral et al. | |
| 2018/0353117 A1* | 12/2018 | Bullington ......... | A61B 5/15003 |
| 2019/0314614 A1 | 10/2019 | Krause et al. | |
| 2019/0314615 A1 | 10/2019 | Johnson et al. | |
| 2019/0357892 A1 | 11/2019 | Abitabilo et al. | |
| 2020/0009366 A1 | 1/2020 | Abitabilo et al. | |

OTHER PUBLICATIONS

Extended European Search Report corresponding to EP 19816032 dated Feb. 24, 2022.

* cited by examiner

BLOOD SEQUESTRATION DEVICE AND METHOD

RELATED APPLICATIONS

This application is a continuation of application Ser. No. 16/434,284 filed Jun. 7, 2019, which claims the benefit of U.S. Provisional Application No. 62/682,362 filed Jun. 8, 2018, each of which is hereby incorporated herein in its entirety by reference.

TECHNICAL FIELD

The present disclosure relates generally to a device for accessing the bloodstream of a patient, and more particularly to a device and method for inhibiting potentially contaminated blood from inclusion in a blood culture test sample.

BACKGROUND

A blood culture is the standard test used to detect microbial infections that may be spreading through a patient's bloodstream. The results from a blood culture are used to verify whether or not an infection is present, and, if so, what type (or types) of microorganisms are responsible for the infection. For example, blood cultures can be used to identify the causative microorganisms in severe pneumonia, puerperal fever, pelvic inflammatory disease, neonatal eppiglottitis, sepsis, and fever of unknown origin.

During a blood culture, a sample of blood (typically at least 10 mL) is with withdrawn from the patient, often via peripheral venipuncture, and stored in one or more blood culture bottles with a specific media for aerobic and anaerobic organisms. Often more than one sample is taken from different areas of the patient's body to form a blood culture set. The proper collection of blood samples is a critical part of conducting a blood culture. An improper collection procedure, for example from improper or incomplete disinfection of the skin area in or around the venipuncture site or coring of skin containing microorganisms by the needle during insertion, can result in a contaminated blood sample.

It is estimated that of the millions of blood culture tests performed on patients each year, roughly one-third of the test results indicate the false presence of microorganisms in the patient's bloodstream (i.e., a false positive). That is, even though microorganisms are found in the patient's blood during the test, those microorganisms were mixed with the blood during the venipuncture procedure. As most caregivers presume that the blood collection procedure was performed correctly, clinicians often treat all positive blood cultures (false or not) with antibiotics. On top of increased patient anxiety and the risks associated with overtreatment, as typical antibiotic treatments range from $4,500 to $10,000, it is estimated that false positive blood cultures significantly add to the cost of healthcare.

Although various strategies and devices have been implemented to decrease blood culture contamination rates, to this day the estimated number of false positive blood cultures remains quite high. Applicants of the present disclosure have identified a need for a blood sampling device and method to address this concern.

SUMMARY OF THE DISCLOSURE

Embodiments of the present disclosure provide a device and method configured to isolate an initial (and potentially contaminated) portion of a blood sample before delivering a balance of the blood sample to an evacuated tube or syringe for use in blood culture testing. In some embodiments, an initial quantity of at least 0.15 mL of blood is sequestered in a manner that enables the remaining flow of blood to be diverted to a blood collection device. In some embodiments, the disclosed device passively diverts the remaining flow of blood after the initial quantity of blood has been sequestered with no moving parts. In some embodiments, the disclosed device can be actively shifted between an initial blood sequestration position and a blood collection position. In some embodiments, a sharp distal tip of the disclosed device can be automatically retracted to a safe position to inhibit unwanted needle sticks.

One embodiment of the present disclosure provides a blood sequestration device configured to isolate an initial, potentially contaminated portion of blood from a flow of blood from vasculature of a patient, prior to directing the flow of blood to an outlet support where the blood can be accessed. The blood sequestration device can include a body member having an interior wall defining a generally "Y" shaped fluid conduit having a distal portion, a first proximal portion, and a second proximal portion. The first proximal portion can define an inlet port configured to be fluidly coupled to vasculature of the patient. The second proximal portion can define a sequestration chamber configured to isolate an initial portion of blood of a flow of blood, and a vent path configured to enable the escape of gas initially trapped within the sequestration chamber. The first proximal portion can be axially aligned with a longitudinal axis of the distal portion. The second proximal portion can define a fluid path and an outlet port configured to be fluidly coupled to a blood collection device. The second proximal portion can be offset from the longitudinal axis of the distal portion by an oblique angle.

In one embodiment axial alignment of the first proximal portion with the distal portion promotes an initial flow of blood into the sequestration chamber. In one embodiment, the vent path includes a gas permeable membrane configured to enable gas initially trapped within the sequestration chamber to vent from the sequestration chamber as blood fills the sequestration chamber. In one embodiment, the outlet port is initially sealed, thereby trapping gas within the second proximal portion, such that a natural pressure of the trapped gas inhibits a flow of blood into the second proximal portion. In one embodiment, the outlet port can include a needle free connector shiftable from a naturally biased closed position to an open position upon the insertion of a Luer taper. In one embodiment, the flow of blood into the second proximal portion is inhibited via a blood collection device. In one embodiment, the outlet port defines a Luer connector. In one embodiment, the oblique angle between the second proximal portion and the distal portion is configured to enable a smooth flow of blood past an opening into the sequestration chamber and into the second proximal portion. In one embodiment, the sequestration chamber has a volume of at least 0.15 mL. In one embodiment, the device further comprises a portion of flexible tubing in fluid communication with the first proximal portion defining at least a portion of the sequestration chamber.

Another embodiment of the present disclosure provides a blood sequestration device configured to isolate an initial portion of blood from a flow of blood of the patient, prior to directing the flow of blood to an outlet port. The blood sequestration device can include a body member having an interior wall defining a fluid conduit having an inlet port, a vented sequestration chamber, a restricted flow path portion positioned between the inlet port and the vented sequestration chamber, and a side outlet port positioned between the inlet port and the restricted flow path portion. The side outlet port can be initially sealed, such that a flow of blood entering the inlet port can follow a path of least resistance to the vented sequestration chamber, where an initial portion of blood can be isolated at least in part by the restricted flow path portion.

In one embodiment, the restricted flow path portion can be defined by a flow restrictor element positioned within the fluid conduit. In one embodiment the vented sequestration chamber can include a gas permeable membrane configured to enable the gas initially trapped within the vented sequestration chamber to vent from the vented sequestration chamber as the initial portion of blood fills the vented sequestration chamber. In one embodiment, sealing the outlet port can cause a natural pressure of gas trapped in proximity to the outlet port to inhibit a flow of blood into the outlet port. In one embodiment, the outlet port can include a needle free connector shiftable from a naturally biased closed position to an open position upon the insertion of a Luer taper. In one embodiment a flow of blood into the second proximal portion is inhibited via a blood collection device. In one embodiment, the outlet port defines a Luer connector. In one embodiment the vented sequestration chamber has a volume of at least 0.15 mL.

Another embodiment of the present disclosure provides a blood sequestration device configured to isolate an initial portion of blood from a flow of blood of a patient, prior to directing the flow of blood to an outlet port. The blood sequestration device can include a body member and an elastomeric blood control valve. The body member can have an inlet port, a vented sequestration chamber, and an outlet port. The vented sequestration chamber can be configured to isolate an initial portion of blood from the flow of blood while enabling the escape of gas trapped within the vented sequestration chamber. The elastomeric blood control valve can be positioned between the inlet port and the outlet port and can be movable between an initial, closed position, where the elastomeric blood control valve inhibits a flow of blood from the inlet port to the output port, and an open position, where the elastomeric blood control valve permits the flow of blood from the inlet port to the outlet port.

In one embodiment, the vented sequestration chamber includes a gas permeable membrane configured to enable gas initially trapped within the vented sequestration chamber to vent from the vented sequestration chamber as the initial portion of blood fills the vented sequestration chamber. In one embodiment, the vented sequestration chamber is operably coupled to a side port positioned between the inlet port and the outlet port of the body member. In one embodiment, sealing the outlet port causes a natural pressure of gas trapped in proximity to the outlet port to inhibit a flow of blood into the outlet port. In one embodiment, the outlet port defines a Luer connector. In one embodiment the vented sequestration chamber has a volume of at least 0.15 mL.

Another embodiment of the present disclosure provides a blood sequestration device configured to automatically retract and safely house a sharpened distal tip of the needle following the isolation of an initial portion of blood and collection of a subsequent sample of blood from a flow of blood of the patient. The blood sequestration device can include a needle, a sequestration body, a needle housing, and a biasing mechanism. The needle can have a sharpened distal tip, a proximal end, and a wall defining a lumen therebetween. The sequestration body can have an inlet port operably coupled to the proximal end of the needle, a vented sequestration chamber in fluid communication with the lumen of the needle and configured to isolate an initial portion of blood from a flow of blood while enabling escape of gas trapped within the sequestration chamber, and an outlet port configured to be fluidly coupled to a blood collection device for the collection of a subsequent sample of blood from the flow of blood. The needle housing can be configured to selectively house the sharpened distal tip of the needle in a safe position. The biasing mechanism can be positioned between the sequestration body and the needle housing, and can be configured to bias the needle from an initial, blood collection position to the safe position, in which the sharpened distal tip of the needle is housed within the needle housing.

In one embodiment, the sequestration body can include one or more wings. In one embodiment the sequestration body can include a guide lock, and the needle housing can define a channel in which the guide lock is configured to traverse. In one embodiment, the guide lock is configured to selectively lock the sequestration body relative to the needle housing against the bias of the biasing mechanism in the blood collection position. In one embodiment, rotation of the sequestration body relative to the needle housing enables automatic withdrawal of the sharpened distal tip of the needle into the needle housing.

Another embodiment of the present disclosure provides a blood sequestration device configured to automatically retract and safely house a sharpened distal tip of the needle following the isolation of an initial portion of blood and collection of a subsequent sample of blood from a flow of blood of a patient. The blood sequestration device can include a housing, needle, needle biasing mechanism, and movable element. The needle can be operably coupled to the housing, and can include a sharpened distal tip, proximal end, and wall defining a lumen therebetween. The needle biasing mechanism can be operably coupled to the proximal end of the needle and can be configured to bias the needle from an initial position, in which the sharpened distal tip of the needle protrudes from the housing, to a safe position, in which the sharpened distal tip of the needle is housed within the housing. The movable element can be shiftable within the housing between an initial blood sequestration position, a blood collection position, and a needle retraction position. The movable element can define a sequestration chamber, a fluid conduit for blood collection, and a chamber configured to retain the needle in the safe position.

In one embodiment, the movable element can define one or more push tabs configured to protrude from the housing to enable user manipulation of the movable element relative to the housing between the initial blood sequestration position, blood collection position, and needle retraction position. In one embodiment, user manipulation of the one or more push tabs in the first direction can cause the movable element to shift from the initial blood sequestration position to the blood collection position. In one embodiment, further user manipulation of the one or more push tabs in the first direction can cause the movable element to shift from the blood collection position to the needle retraction position. In one embodiment, the movable element can define a first push tab and a second push tab configured to protrude from the housing to enable user manipulation of the movable element relative to the housing between the initial blood sequestration position, blood collection position, and needle retraction position. In one embodiment, user manipulation of the first push tab in a first direction causes the movable element to shift from the initial blood sequestration position to the blood collection position. In one embodiment, user manipulation of the second push tab in a second direction causes the movable element to shift from the blood collection position to the needle retraction position. In one embodiment, the sequestration chamber includes a gas permeable membrane configured to enable the gas initially trapped within the sequestration chamber to vent from the sequestration chamber as the initial portion of blood of the flow of blood fills the sequestration chamber. In one embodiment, the fluid conduit for blood collection is operably coupled to a length of flexible tubing configured to be operably coupled to a blood collection device. In one embodiment the fluid conduit for blood collection is occluded upon shifting the movable element to the needle retracted position. In one embodiment, in the needle retracted position, the entire movable element is housed within the housing to inhibit user manipulation of the movable element relative to the housing. In one embodiment, the device further includes a catheter operably coupled to the housing and configured to coaxially ride over the needle for positioning within vasculature of the patient.

Another embodiment of the present disclosure provides a blood sequestration device configured to automatically retract and safely house a sharpened distal tip of a needle following the isolation of an initial portion of blood from a flow of blood from vasculature of the patient. The blood sequestration device can include a housing, needle, needle biasing mechanism, catheter, and movable element. The needle can be operably coupled to the housing, and can include a sharpened distal tip, proximal end, and wall defining a lumen therebetween. The needle biasing mechanism can be operably coupled to the proximal end of the needle and can be configured to bias the needle from an initial position, in which the sharpened distal tip of the needle protrudes from the housing, to a safe position, in which the sharpened distal tip of the needle is housed within the housing. The catheter can be operably coupled to the housing and can be configured to coaxially ride over the needle for positioning within the vasculature of the patient. The movable element can be shiftable within the housing between an initial blood sequestration position and a blood collection position. The movable element can define a sequestration chamber and a chamber configured to retain the needle in the safe position.

In one embodiment, the chamber configured to retain the needle in the safe position can further define a fluid conduit for blood collection. In one embodiment, the fluid conduit for blood collection is operably coupled to a length of flexible tubing configured to be operably coupled to a blood collection device. In one embodiment, the movable element can define one or more push tabs configured to protrude from the housing to enable user manipulation of the movable element relative to the housing between the initial blood sequestration position and the blood collection position. In one embodiment, user manipulation of the one or more push tabs cause the movable element to shift from the initial blood sequestration position to the blood collection position, wherein the needle is retracted into the safe position. In one embodiment, the sequestration chamber includes a gas permeable membrane configured to enable gas initially trapped within the sequestration chamber to vent from the sequestration chamber as the initial portion of blood of the flow of blood fills the sequestration chamber. In one embodiment, in the blood collection position the entire movable element is housed within the housing to inhibit user manipulation of the movable element relative to the housing.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figures 1A, 1B, 1C:
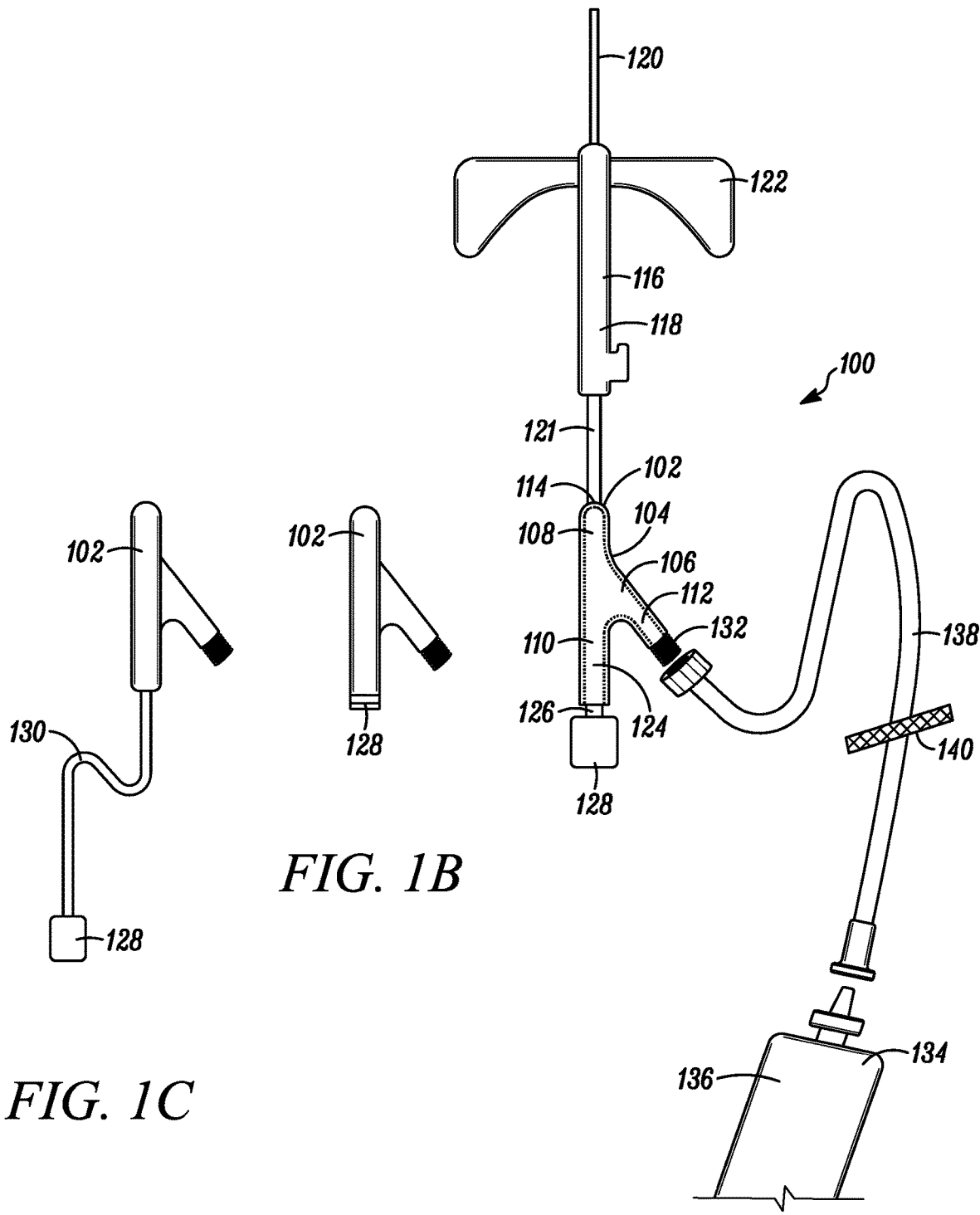
FIG. 1A is a plan view depicting a blood sequestration device in accordance with a first embodiment of the disclosure.
FIG. 1B is a plan view depicting a first alternate body member in accordance with the first embodiment of the disclosure.
FIG. 1C is a plan view depicting a second alternate body member in accordance with the first embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Various blood sequestration devices are described herein for use in accessing the vein of a subject. It is to be appreciated, however, that the example embodiments described herein can alternatively be used to assess the vasculature of a subject at locations other than a vein, including but not limited to the artery of a subject. It is additionally to be appreciated that the term "caregiver,"

"clinician," or "user" refers to any individual that can collect a blood sample for blood culture analysis with any of the example embodiments described herein or alternative combinations thereof. Similarly, the term "patient" or "subject," as used herein is to be understood to refer to an individual or object in which the blood sequestration device is utilized, whether human, animal, or inanimate. Various descriptions are made herein, for the sake of convenience, with respect to the procedures being performed by a clinician to access the vein of the subject, while the disclosure is not limited in this respect.

It is also to be appreciated that the term "distal," as used herein refers to the direction along a longitudinal axis of the blood sequestration device that is closest to the subject during the collection of a blood sample. Conversely, the term "proximal," as used herein, refers to the direction lying along the longitudinal axis of the blood sequestration device that is further away from the subject during the collection of a blood sample, opposite to the distal direction.

Referring to FIG. 1A, a plan view of a blood sequestration device 100 is depicted in accordance with a first embodiment of the disclosure. In one embodiment, the blood sequestration device 100 can include a body member 102 having an interior wall 104 defining a generally "Y" shaped fluid conduit 106. The fluid conduit 106 can include a distal portion 108, a first proximal portion 110, and a second proximal portion 112.

The distal portion 108 can include an inlet port 114 configured to be fluidly coupled to vasculature of a patient. For example, in one embodiment, the inlet port 114 can be in fluid communication with a catheter assembly 116. The catheter assembly 116 can include a catheter hub 118 and a catheter tube 120. In one embodiment, the catheter tube 120 can extend from a tapered distal end to a proximal end, where the catheter tube 120 can be operably coupled to the catheter hub 118. The catheter tube 120 can define a lumen configured to provide a fluid pathway between a vein of the subject and the catheter hub 118. In one embodiment, the catheter tube 120 can include a barium radiopaque line to ease in the identification of the catheter tube 120 during radiology procedures. In an alternative embodiment, the catheter tube 120 can include a metallic radiopaque line, or any other suitable radiopaque material. The catheter hub 118 can include a catheter hub body having a distal end, a proximal end and an internal wall defining an interior cavity therebetween. The interior cavity can include a proximal portion extending from an open proximal end, and a distal portion in proximity to the distal end. In one embodiment, the distal end of the catheter hub body is operably coupled to the proximal end of the catheter tube 120, such that the lumen of the catheter tube is in fluid communication with the proximal portion of the interior cavity.

In some embodiments, the catheter assembly 116 can further include an extension tube 121 operably coupling the catheter assembly 116 to the blood sequestration device 100. In other embodiments, the blood sequestration device 100 can be directly coupled to the catheter assembly 116 and/or the blood sequestration device 100 and the catheter assembly 116 can be formed as a unitary member. Some embodiments of the catheter assembly 116 can further include a wing assembly 122 configured to aid a clinician in gripping, maneuvering and/or securing of the catheter assembly 116 to the patient during the collection of a blood sample.

The first proximal portion 110 can define a sequestration chamber 124 configured to isolate an initial quantity of blood during the collection of a blood sample for blood culture analysis. For example, in one embodiment, blood from the vasculature of the patient under normal pressure can flow into and fill the sequestration chamber 124, thereby displacing a quantity of gas initially trapped within the sequestration chamber 124.

The first proximal portion 110 can include a vent path 126 configured to enable the escape of the gas initially trapped within the sequestration chamber 124, while inhibiting the escape of blood. For example, in one embodiment, the vent path 126 can be sealed at one end by a plug 128. The plug 128 can be made out of an air permeable, hydrophilic material that enables the passage of air, but inhibits the passage of liquid. For example, in one embodiment, the plug 128 can include a plurality of pores shaped and sized to enable the passage of low-pressure gas, but inhibit the passage of low-pressure fluid, such that the pores of the plug 128 become effectively sealed upon contact with the low-pressure fluid. Air that resides within the sequestration chamber 124 is therefore pushed through the plug 128 by the incoming blood, until the blood reaches the plug 128 or is otherwise stopped.

In one embodiment, the plug 128 can be inserted into the vent path 126 (as depicted in FIG. 1A). For example, in one embodiment, the vent path 126 can define a Luer connector configured to accept a portion of the plug 128. In another embodiment, the vent plug 128 can be adhered to the body member 102, so as to occlude the vent path 126 (as depicted in FIG. 1B). Alternatively, the vent plug 128 can be shaped and sized to fit within the first proximal portion 110 of the fluid conduit 106 at a proximal end of the sequestration chamber 124. In yet another embodiment, the plug 128 can be operably coupled to an extension tube 130, which can be operably coupled to the distal end of the first proximal portion, (as depicted in FIG. 1C) such that an interior volume of the extension tubing defines at least a portion of the sequestration chamber, thereby enabling the increase of the internal capacity of the sequestration chamber 124. In one embodiment, the sequestration chamber 124 has a volume of at least 0.15 mL, although other volumes of the sequestration chamber 124 are also contemplated.

In some embodiments, a longitudinal axis of the first proximal portion 110 of the fluid conduit 106 can be axially aligned with a longitudinal axis of the distal portion 108 of the fluid conduit 106. In this manner, the axial alignment of the first proximal portion 110 with the distal portion 108 can promote an initial flow of blood into the sequestration chamber 124.

In some embodiments, the body member 102 of the blood sequestration device 100 can be constructed of a clear or translucent material configured to enable a clinician to view the presence of blood within the sequestration chamber 124. In this respect, the clinician can monitor the proper isolation of an initial portion of blood during the collection of a blood sample for blood culture analysis.

The second proximal portion 112 can define a fluid path and an outlet port 132 configured to be fluidly coupled to a blood collection device 134. For example, in one embodiment, the outlet port 132 can define a Luer connector configured to accept a portion of the blood collection device 134. In other embodiments, the outlet port 132 can define a threaded portion configured to be threadably coupled to a portion of the blood collection device 134.

In some embodiments, the blood collection device 134 can be a vial or syringe 136 fluidly coupled to the outlet port 132 by an extension tube 138. In some embodiments, the flow of blood into the second proximal portion 112 can be inhibited by the blood collection device 134. For example, in one embodiment, the blood collection device 134 can include a clamp 140 configured to occlude the extension tube 138 and/or inhibit the venting of an initial quantity of gas present in the second proximal portion 112 and portions of the blood collection device 134, such that a natural pressure of the trapped gas within the second proximal portion 112 inhibits a flow of blood into the second proximal portion 112.

In some embodiments, a longitudinal axis of the second proximal portion 112 of the fluid conduit 106 can be at an oblique angle to a longitudinal axis of the distal portion 108 of the fluid conduit 106. In this manner, the oblique angle of the second proximal portion 110 can enable a smooth flow of blood past an opening into the sequestration chamber 124 and into the second proximal portion 112, once the sequestration chamber 124 has been filled with the initial quantity of blood for isolation.

Figure 2B:
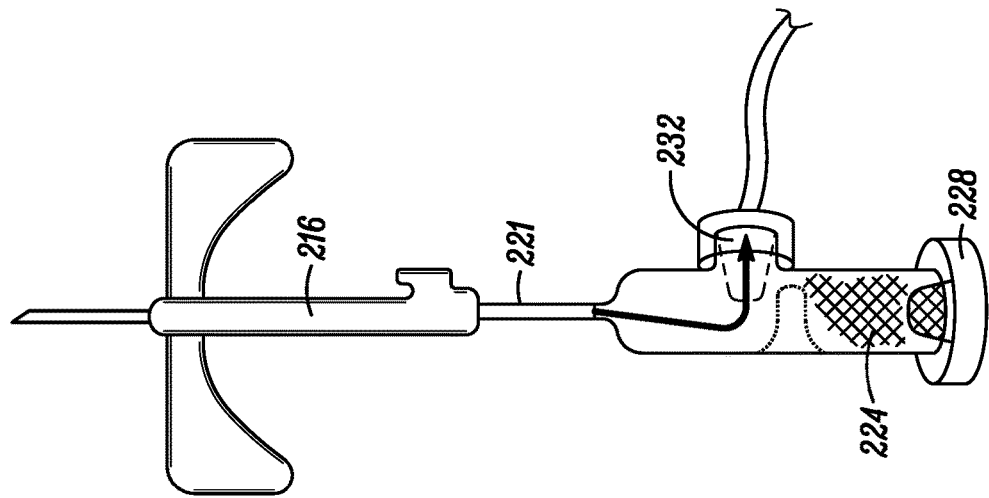
FIGS. 2A-B are plan views depicting a blood sequestration device in accordance with a second embodiment of the disclosure.
Figure 2A:
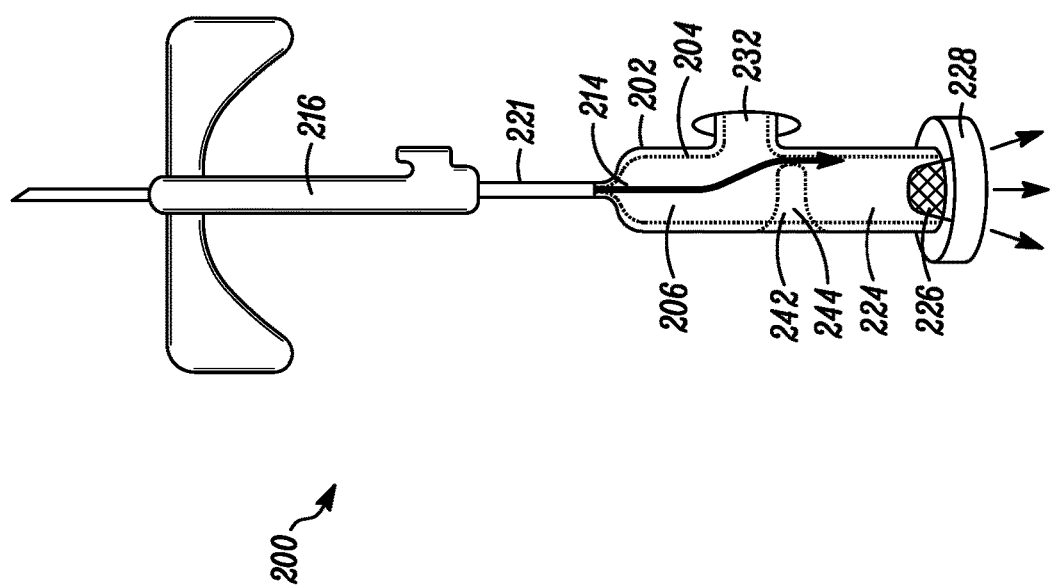

Referring to FIGS. 2A-B, a blood sequestration device 200 is depicted in accordance with a second embodiment of the disclosure. The blood sequestration device 200 can include a body member 202 having an interior wall 204 defining a fluid conduit 206. The fluid conduit 206 can define an inlet port 214, a vented sequestration chamber 224, and an outlet port 232.

The inlet port 214 can be configured to be fluidly coupled to vasculature of a patient. For example, in one embodiment, the inlet port 214 can be in fluid communication with a catheter assembly 216. In some embodiments, the blood sequestration device 200 can be operably coupled to the catheter assembly 216 by an extension tube 221. In other embodiments, the blood sequestration device 200 can be directly coupled to the catheter assembly 216 and/or the blood sequestration device 200 and the catheter assembly 216 can be formed as a unitary member. Some embodiments of the catheter assembly 216 can further include a wing assembly configured to aid a clinician and gripping, maneuvering, and/or securing of the catheter assembly to the patient during the collection of a blood sample.

The vented sequestration chamber 224 can be configured to isolate an initial quantity of blood during the collection of a blood sample. For example, in one embodiment, blood from the vasculature of the patient under normal pressure can flow into and fill the vented sequestration chamber 224, thereby displacing a quantity of gas initially trapped within the sequestration chamber 224. The vented sequestration chamber 224 can include a vent path 226 sealed by an air permeable, hydrophilic material plug 228 configured to enable the passage of air, but inhibit the passage of liquid. Accordingly, air that resides within the vented sequestration chamber 224 can be pushed through the plug 228 by the incoming blood, until the blood reaches the plug 228 or is otherwise stopped.

The outlet port 232 can be positioned between the inlet port 214 and the vented sequestration chamber 224. In one embodiment, the outlet port 232 can be positioned on a side wall of the body member 202, substantially orthogonal to a longitudinal axis of the inlet port 214 and/or the sequestration chamber 224.

In some embodiments, the interior wall 204 of the fluid conduit 206 can define a restricted flow path portion 242 configured to aid in the isolation of an initial quantity of blood within the vented sequestration chamber 224. In some embodiments, the restricted flow path portion 242 is defined by contours of the interior wall 204 of the fluid conduit. In other embodiments, the restricted flow path portion 242 is defined by a separate flow restrictor element 244 positioned within the fluid conduit 206 (as depicted in FIGS. 2A-3B).

Figure 3B:
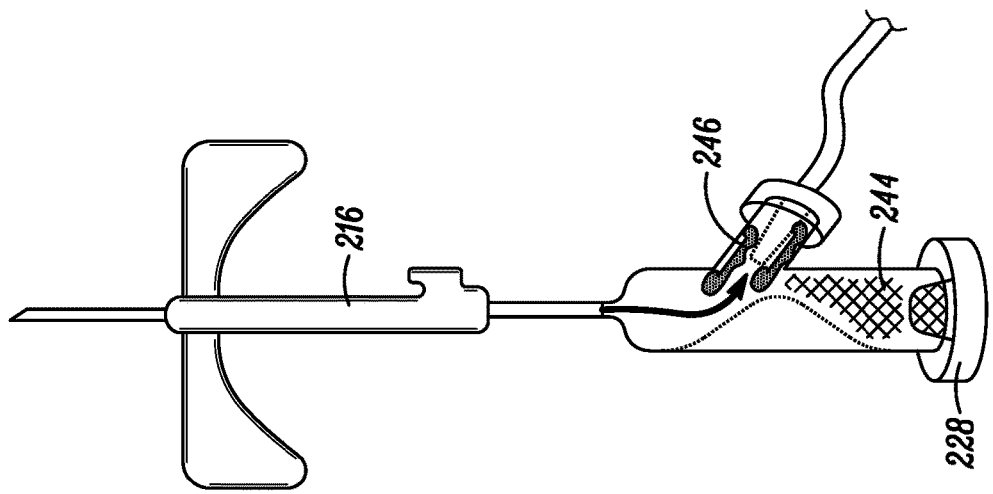
FIGS. 3A-B are plan views depicting a first alternate blood sequestration device in accordance with the second embodiment of the disclosure.
Figure 3A:
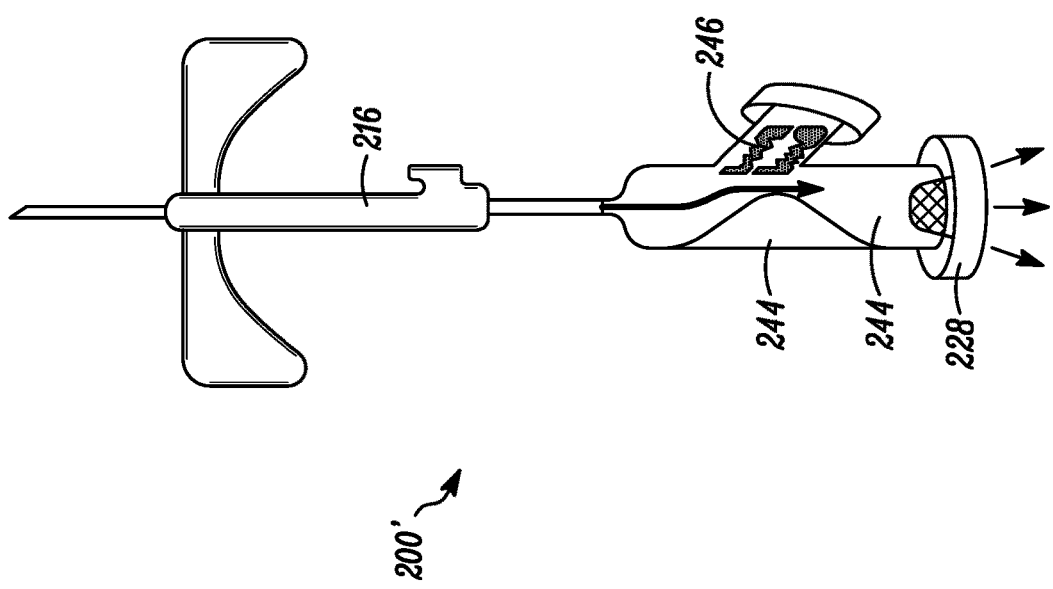

In some embodiments, the outlet port 232 can be initially sealed during the collection of a sample of blood, such that a flow of blood entering the inlet port 214 naturally follows a path of least resistance into the vented sequestration chamber 224, where an initial quantity of blood can be isolated. Accordingly, in one embodiment, sealing of the outlet port 232 causes a natural pressure of gas trapped in proximity to the outlet port 232 to inhibit a flow of blood into the outlet port 232. In one embodiment, the outlet port 232 can define a Luer connector configured to accept a portion of a blood collection device 234. The blood collection device 234 can be configured to occlude the outlet port 232, so as to inhibit the flow of blood into the outlet port 232 and encourage the natural flow of an initial quantity of blood into the vented sequestration chamber 224. In one embodiment, the outlet port 232 can include a needle free connector 246 shiftable from a naturally biased close position to an open position upon the insertion of a Luer taper (as depicted in FIGS. 3A-B).

Figure 4B:
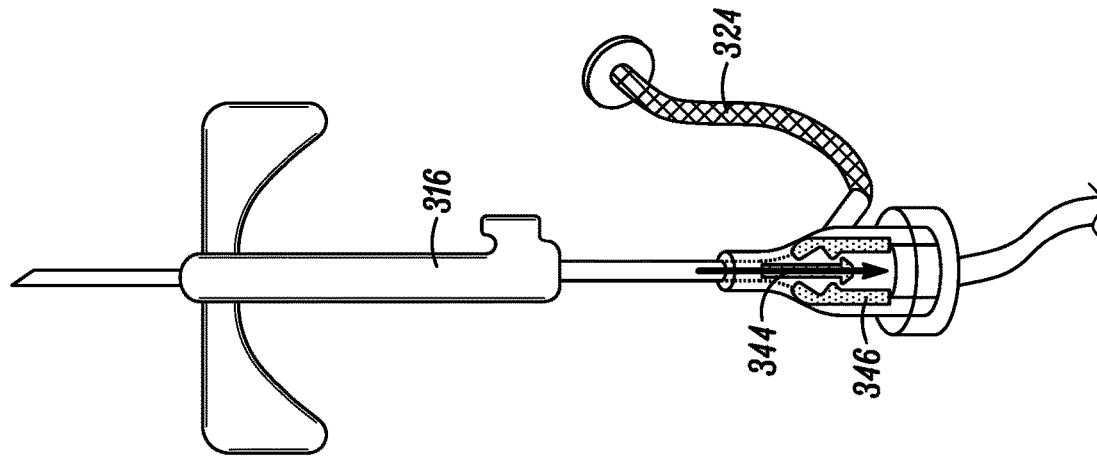
FIGS. 4A-B are plan views depicting a blood sequestration device in accordance with a third embodiment of the disclosure.
Figure 4A:
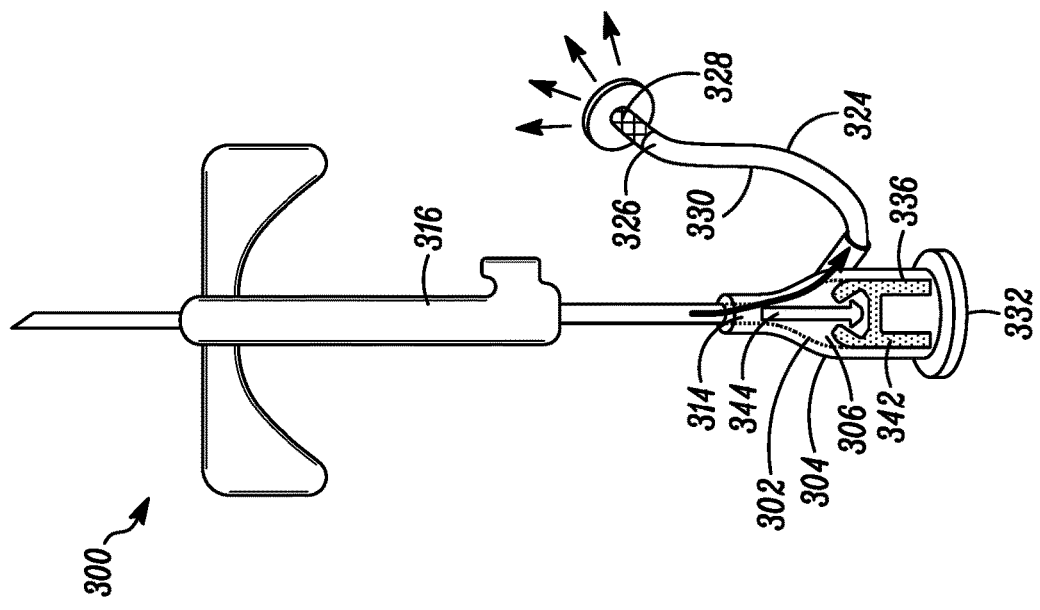

Referring to FIGS. 4A-B, a blood sequestration device 300 is depicted in accordance with a third embodiment of the disclosure. The blood sequestration device 300 can include a body member 302 and an elastomeric blood control valve 342. The body member 302 can include an interior wall 304 defining a fluid conduit 306 having an inlet port 314, a vented sequestration chamber 324, and an outlet port 332.

The inlet port 314 can be configured to be fluidly coupled to a vein of a patient, so as to enable a flow of blood from vasculature of the patient to flow into the fluid conduit 306 of the blood sequestration device 300. For example, in one embodiment, the inlet port 314 can be fluidly coupled to a catheter assembly 316.

The vented sequestration chamber 324 can be configured to isolate an initial quantity of blood during the collection of a blood sample. For example, in one embodiment, blood from the vasculature of the patient under normal pressure can flow into and fill the vented sequestration chamber 324, thereby displacing a quantity of gas initially trapped within the sequestration chamber 324. The vented sequestration chamber 324 can include a vent path 326 sealed by an air permeable, hydrophilic material plug 328 configured to enable the passage of air, but inhibit the passage of liquid.

In one embodiment, the vented sequestration chamber 324 can be positioned between the inlet port 314 and the outlet port 332. In one embodiment, the vented sequestration chamber 324 can extend from a side wall of the body member 302 at an oblique angle relative to a longitudinal axis of the inlet port 314 and/or the outlet port 332. In another embodiment, the vented sequestration chamber 324 can extend from the side wall of the body member 302 substantially orthogonal to a longitudinal axis of the inlet port 314 and/or outlet port 332. In some embodiments, a portion of the vented sequestration chamber 324 can be defined by a length of flexible hollow tubing 330. In some embodiments, the vented sequestration chamber has a volume of at least 0.15 mL, although other volumes of the vented sequestration chamber 324 are also contemplated.

The elastomeric blood control valve 342 can be positioned between the inlet port 314 and the outlet port 332. The elastomeric blood control valve 342 can be configured to move from an initial, closed position (as depicted in FIG. 4A) to inhibit a flow of blood from the inlet port 314 to the outlet port 332, to an open position (as depicted in FIG. 4B) where the elastomeric blood control valve 342 permits the flow of blood from the inlet port 314 to the outlet port 332. In the initial, closed position a natural pressure of gas trapped in proximity to the outlet port 332 inhibits a flow of blood into the outlet port, such that blood naturally flows into the vented sequestration chamber 324. Upon shifting the blood control valve 342 to the open position, the blood flow will follow the path of least resistance to exit the blood sequestration device 300 at the outlet port 332, to which a blood collection device can be operably coupled. Further, when the blood control valve 342 is in the open position, the blood control valve 342 is arranged such that the vented sequestration chamber 324 is sealed from fluid communication with the fluid conduit 306.

In one embodiment, the elastomeric blood control valve 342 can include an actuator 344 secured to the interior wall 304 of the body member 302, so as to extend axially within the fluid conduit 306. The actuator 344 can be a rigid, hollow member configured to enable fluid to pass therethrough. The elastomeric blood control valve 342 can further include a seal member 346 secured within the fluid conduit 306 of the body member 302 with the aid of the actuator 344, such that the seal member 346 is axially shiftable relative to the actuator 344 between the closed position in which flow of fluid through the blood control valve 342 is inhibited or restricted, and the open position, in which the seal member 346 is shifted relative to the actuator 344, thereby enabling the flow of fluid from the inlet port 314, through the elastomeric blood control valve 342, and out through the outlet port 332. One example of such a blood control valve is disclosed in U.S. Pat. No. 9,545,495, the contents of which are incorporated by reference herein.

Figure 5A:
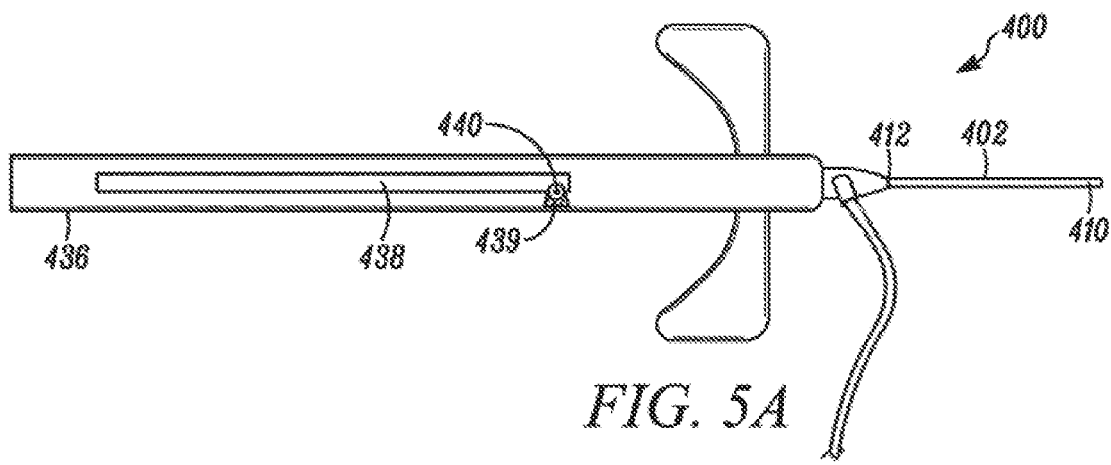
FIG. 5A is a plan view depicting a blood sequestration device in accordance with a fourth embodiment of the disclosure.
Figure 5B:
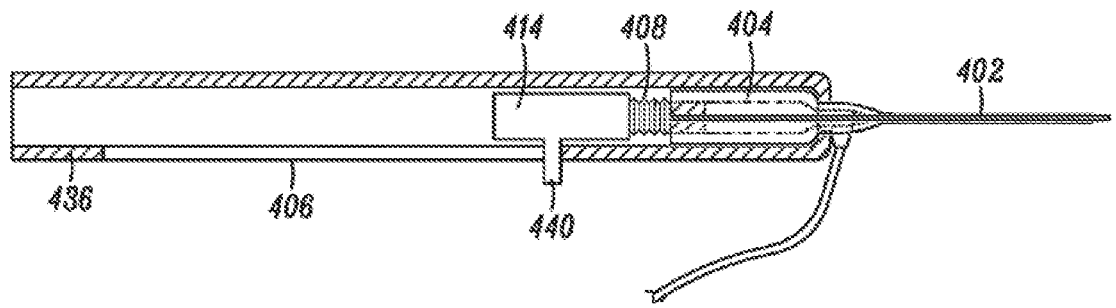
FIG. 5B is a cross-sectional view depicting the blood sequestration device of FIG. 5A.
Figure 5C:
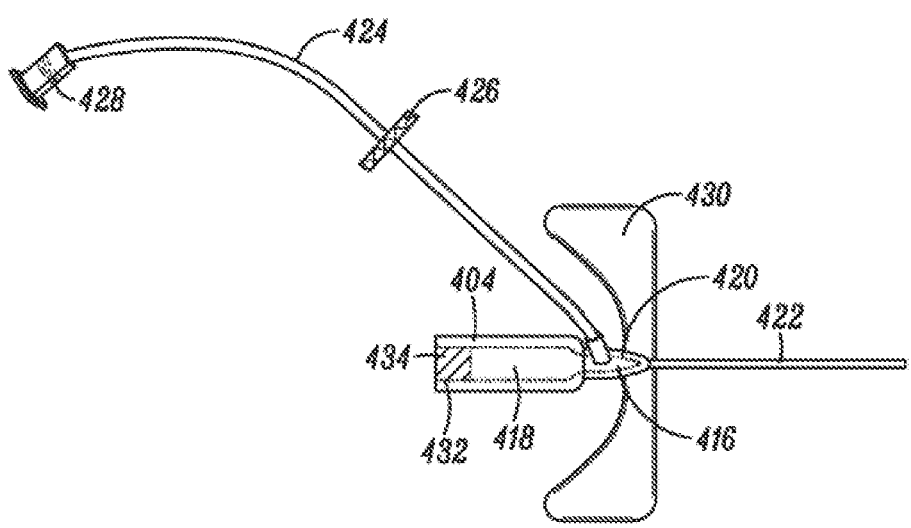
FIG. 5C is a partial cross sectional view depicting a catheter and blood sequestration chamber of a blood sequestration device in accordance with the fourth embodiment of the disclosure.

Referring to FIGS. 5A-C, a blood sequestration device 400 is depicted in accordance with a fourth embodiment of the disclosure. The blood sequestration device 400 can be configured to automatically retract and safely house a sharpened distal tip of the needle following the isolation of an initial quantity of blood during the collection of a blood sample. The blood sequestration device 400 can include a needle 402, a sequestration body 404, a needle housing 406, and a biasing mechanism 408.

The needle 402 can include an elongate cylindrically shaped metal structure defining a lumen that extends between a sharpened distal tip 410 and a proximal end 412. The sharpened distal tip 410 can be constructed and arranged to pierce the skin of the subject during needle insertion. For example, in one embodiment, the sharp distal tip 410 can include a V-point designed to reduce the penetration force used to penetrate the needle 402 and a portion of the sequestration body 404 through the skin, tissue, and vein wall of a subject. In one embodiment, the length of the needle 402 can be extended to aid in accessing vasculature of obese patients.

The proximal end 412 of the needle 402 can be operably coupled to a needle hub 414. In some embodiments, the needle 402 and needle hub 414 can be collectively referred to as a needle assembly. In one embodiment, the needle hub 414 can be constructed to provide a visual indication of a flashback when the sharpened distal tip 410 of the needle 402 enters the vein of the subject. For example, in one embodiment, the needle hub 414 can define a flash chamber in communication with the lumen of the needle 402.

The sequestration body 404 can coaxially ride over at least a portion of the needle 402. In one embodiment, the sequestration body 404 can include a catheter portion 416 and a sequestration chamber 418. The catheter portion 416 can include a catheter hub 420 and a catheter tube 422. The catheter tube can extend from a distal taper end to a proximal end, where the catheter tube 422 can be operably coupled to the catheter hub 420. The catheter tube 422 can define a lumen configured to provide a fluid pathway between a vein of the subject and the catheter hub 420. In one embodiment, the catheter tube 422 can include a barium radiopaque line to ease in the identification of the catheter tube 422 during radiology procedures.

The catheter hub 420 can include a catheter hub body having a distal end, a proximal end, and an internal wall defining an interior cavity therebetween. The interior cavity can include a proximal portion extending from an open proximal end, and a distal portion in proximity to the distal end. In one embodiment, the distal end of the catheter hub body can be operably coupled to the proximal end of the catheter tube 422, such that the lumen of the catheter tube is in fluid communication with the proximal portion of the interior cavity.

In some embodiments, the catheter portion 416 can further comprise a closed catheter assembly, including an extension tube 424, an extension tube clamp 426, and a needleless connector 428. Alternatively, the interior wall defining the interior cavity of the catheter hub 420 can further define a side port (not depicted) configured to enable an alternative fluid communication path with the interior cavity of the catheter hub 420. In one embodiment, the side port can be positioned substantially orthogonal to a longitudinal axis of the catheter hub 420. The side port can be selectively sealed by a flexible sealing member position within the interior cavity of the catheter hub 420. Some embodiments can further include a wing assembly 430 configured to aid a clinician and gripping, maneuvering and/or securing the sequestration body 404 to the subject during the collection of a blood sample.

The sequestration chamber 418 can be configured to isolate an initial quantity of blood during the collection of a blood sample. In one embodiment, the sequestration chamber 418 can have a distal end, a proximal end, and an internal wall defining an interior cavity therebetween. The distal end of the sequestration chamber 418 can be operably coupled to the proximal and the catheter hub 420, such that interior cavities of the catheter hub 420 and sequestration chamber 418 are in fluid communication.

The proximal end of the sequestration chamber 418 can define a vent path 432 configured to enable the escape of gas initially trapped within the sequestration chamber 418, while inhibiting the escape of blood. For example, in one embodiment, the vent path 432 can be sealed at one end by a valve or septum 434. In one embodiment, the septum 434 can be configured to enable at least a portion of the needle 402 to pass therethrough during insertion of the catheter tube 422 into the vein of the subject. The septum 434 can be configured to seal upon withdrawal of the needle 402 through the septum 432, thereby inhibiting the leakage of blood after the needle 402 has been withdrawn. In one embodiment, the septum can further be made out of an air permeable, hydrophilic material configured to enable the passage of air, but inhibit the passage of liquid, thereby enabling air that resides within the sequestration chamber 418 to be evacuated through the septum 432 by the incoming initial quantity of blood to be sequestered.

The needle housing 406 can have a distal end, a proximal end, and a housing wall 436 defining a needle housing cavity therebetween. The needle housing cavity can be shaped and sized to accommodate at least a portion of the needle hub 414 there within. The needle hub 414 can be slidably coupled to the needle housing 406 between an initial, blood collection position (as depicted in FIG. 5B), in which at least a portion of the needle 402 extends beyond the needle housing 406, and a safe position, in which the sharpened distal tip 410 of the needle 402 is housed within the needle housing 406.

The biasing mechanism 408 can be operably coupled between the needle hub 414 and the distal end of the needle housing 406, and can be configured to naturally bias the needle hub 414 to the safe position. In one embodiment, the biasing mechanism 408 can be a coil spring, although other biasing mechanisms are also contemplated. The needle housing wall 436 can further define a channel 438 including a blood collection position notch 439, into which a guide lock 440 of the needle hub 414 can extend. In some embodiments, rotation of the needle hub 414 relative to the needle housing 406 about its longitudinal axis can cause the guide lock 440 to rotate out of the blood collection position notch 439, such that the natural bias of the biasing mechanism 408 can shift the needle hub 414 to the safe position, wherein the needle hub 414 is guided by the guide lock 440 of the needle hub 414 to traverse along a length of the channel 438.

Referring to FIGS. 6A-D, a blood sequestration device 500 is depicted in accordance with a fifth embodiment of the disclosure. The blood sequestration device 500 can be configured to automatically retract and safely house a sharpened distal tip of the needle following the isolation of an initial quantity of blood during the collection of a blood sample. The blood sequestration device 500 can include a housing 502, needle 504, needle biasing mechanism 506, and movable element 508.

Figure 6A:
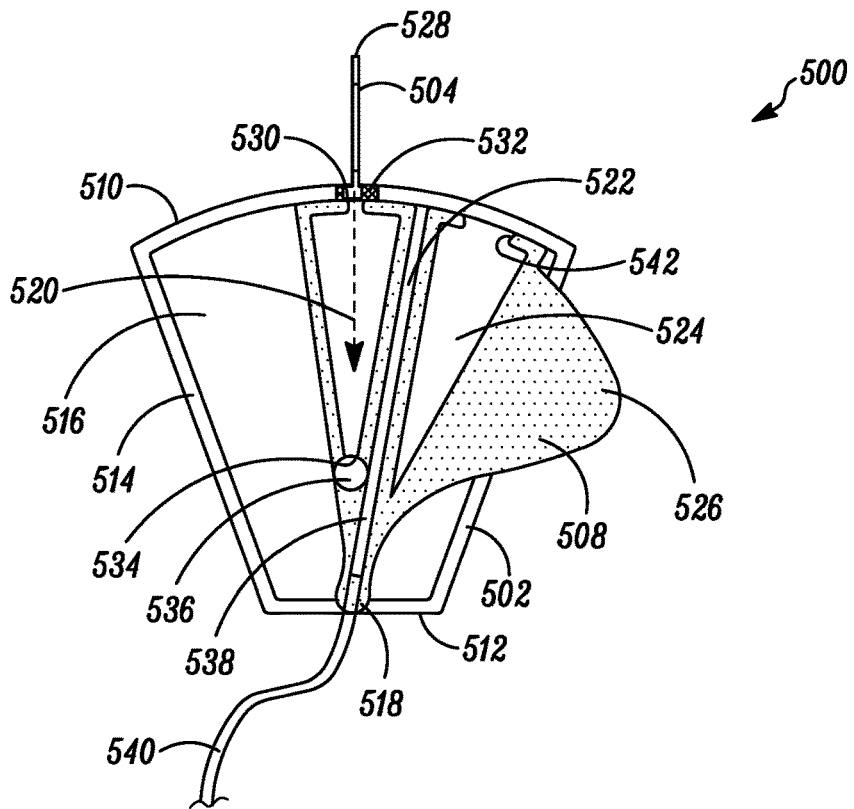
FIGS. 6A-D are plan views a blood sequestration device in accordance with a fifth embodiment of the disclosure.

The housing 502 can have a distal end 510, proximal end 512 and housing wall 514 defining a cavity 516. As depicted in FIG. 6A, in one embodiment, the housing 402 can generally be formed in the shape of a truncated sector, wherein the interior surface of the housing wall 514 along the distal end 510 forms an arc in which points along the interior surface of the housing wall 514 along the distal end 510 are generally equidistant from a point 518 located in proximity to the proximal end 512 of the housing 502.

Figure 6B:
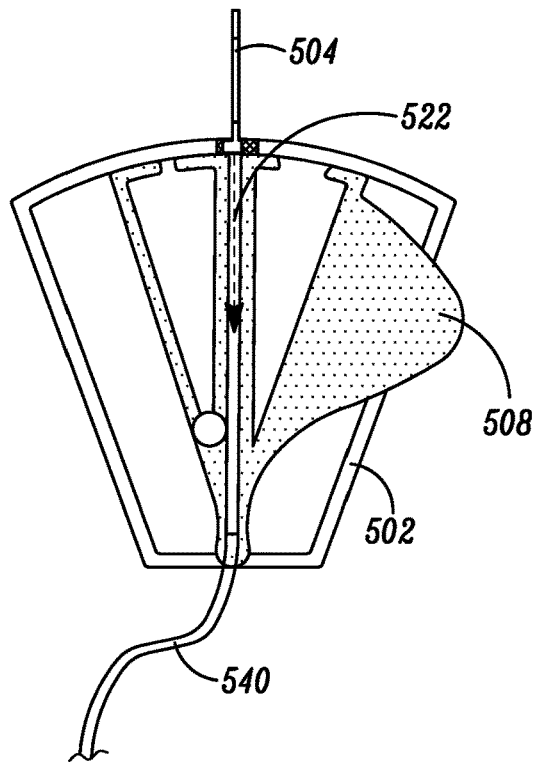
Figure 6C:
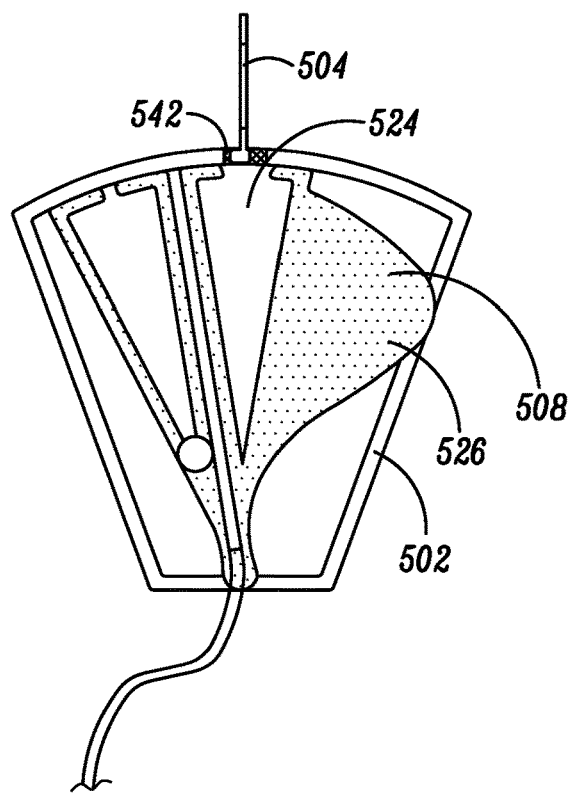
Figure 6D:
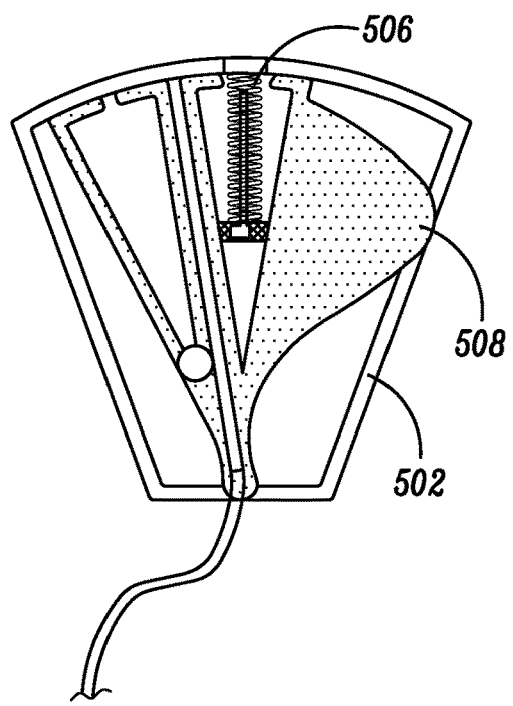

The movable element 508 can reside at least partially within the cavity 516 of the housing 502, and can be pivotably coupled to the housing 502 about point 518, such that the movable element 508 is configured to rotate or shift relative to the housing 502 between an initial blood sequestration position (as depicted in FIG. 6A), a blood collection position (as depicted in FIG. 6B), and a needle retraction position (as depicted in FIG. 6C-D).

In one embodiment, the movable element 508 can define one or more chambers and/or fluid pathways. For example, in one embodiment, the movable element 508 can define a sequestration chamber 520, a blood collection pathway 522, and a chamber 524 configured to house at least a portion of the needle 504 upon retraction. In one embodiment, the movable element 508 can further define one or more push tabs 526 configured to protrude from the housing 502 to enable a clinician to manipulate the movable element 508 relative to the housing 502 between the initial blood sequestration position, blood collection position, and needle retraction position.

The needle 504 can include an elongate cylindrical shaped metal structure defining a lumen that extends between a sharpened distal tip 528 and a proximal end 530. The sharpened distal tip 528 can be constructed and arranged to pierce the skin of the subject during needle insertion. The proximal end 530 of the needle 504 can be operably coupled to a needle hub 532. In some embodiments, the needle 504 and the needle hub 532 can be collectively referred to as a needle assembly.

The needle hub 532 can be slidably coupled to the housing 502 between an initial position (as depicted in FIG. 6A), in which at least a portion of the needle 504 extends beyond the housing 502, and a safe position (as depicted in FIG. 6D), in which the sharpened distal tip 528 of the needle 504 is housed within the housing 502. The biasing mechanism 506 can be operably coupled between the needle hub 532 and the distal end of the housing 502, and can be configured to naturally bias the needle hub 532 to the safe position.

In one embodiment, the blood sequestration device 500 can be provided in the initial blood sequestration position, with the needle 504 extending outwardly from the distal end 510 of the housing 502. Upon insertion of the needle 504 into the vein of a subject, blood flows through the lumen of the needle 504, and into the sequestration chamber 520 defined in the movable element 508.

The sequestration chamber 520 can include a vent path 534 configured to enable the escape of gas initially trapped within the sequestration chamber 520, while inhibiting the escape of blood. For example, in one embodiment, the vent path 534 can be sealed by a plug 536, constructed of an air permeable, hydrophilic material that enables the passage of air, but inhibits the passage of liquid. Air that resides within the sequestration chamber 520 is therefore pushed through the plug 536 by the incoming blood, until the blood reaches the plug 536 or is otherwise stopped. In one embodiment, the sequestration chamber 520 has a volume of at least 0.15 mL, although other volumes of the sequestration chamber 520 are also contemplated.

Once an initial quantity of blood has been sequestered within the sequestration chamber 520, a clinician can manipulate the one or more push tabs 526 to cause the movable element 508 to shift from the initial blood sequestration position to the blood collection position. In the blood collection position, blood can flow from the vein of the subject through the lumen of the needle 504, through the blood collection pathway 522 defined within the movable element 508, and out of the housing 502 through an outlet port 538, which can be operably coupled to a blood collection device via an extension tube 540.

Once a satisfactory quantity of blood has been collected, a clinician can manipulate the one or more push tabs 526 to cause the movable element 508 to shift from the blood sequestration position to the needle retraction position. Prior to movement of the movable element 508 to the needle retraction position, a distal surface of the movable element 508 can inhibit retraction of the needle 504 into the cavity 516 of the housing 502. By contrast, the chamber 524 configured to house at least a portion of the needle 502 upon retraction can include structure defining an opening 542 shaped and sized to enable the needle hub 532 to pass therethrough, thereby enabling the needle 504 to be retracted within the chamber 524 under the natural bias of the needle biasing mechanism 506 to the safe position. In the safe position, the sharpened distal tip 528 of the needle 504 is housed within the chamber 524 to reduce the risk of unintended needle sticks.

In some embodiments, movement of the movable element 508 to the needle retraction position can cause the one or more push tabs to be shifted into the cavity 506 of the housing 502, thereby inhibiting a clinician from further movement of the movable element 508. In one embodiment, movement of the movable element to the needle retraction position can cause a portion of the movable element 508 and/or housing 502 to crimp the extension tube 540, thereby inhibiting leakage of fluid from an attached blood collection device.

In embodiments, the shift between the initial sequestration position (as depicted in FIG. 6A) and the blood collection position (as depicted in FIG. 6B), and the shift from the blood collection position (as depicted in FIG. 6B) to the needle retraction position (as depicted in FIGS. 6C-D) can occur as one fluid motion. In alternative embodiments, an interference protrusion may be introduced within the distal end 510, and within the rotation path of the movable element 508, such that the clinician is aware, via tactile feedback, that the movable element 508 is in the blood collection position and a pause is warranted. In yet other embodiments, a ratchet mechanism can be introduced into pivoting point 518 such that the movable element 508 ceases movement in the blood collection position and the clinician must manipulate the one or more push tabs 526 again to move the movable element 508 from the blood collection position to the needle retraction position.

Referring to FIGS. 7A-D, in some embodiments, the blood sequestration device 500' can include a first push tab 526A and a second push tab 526B configured to protrude from the housing 502 to enable a clinician to manipulate the movable element 508 relative to the housing 502 between the initial blood sequestration position, blood collection position, and needle retraction position. In one embodiment, manipulation of the first push tab 526A in a first direction causes the movable element 508 to shift from the initial blood sequestration position to the blood collection position. Manipulation of the second push tab 526B in a second direction causes the movable element 508 to shift from the blood collection position to the needle retraction position. Other configurations of push tabs 526 defined by the movable element 508 are also contemplated.

Figure 7A:
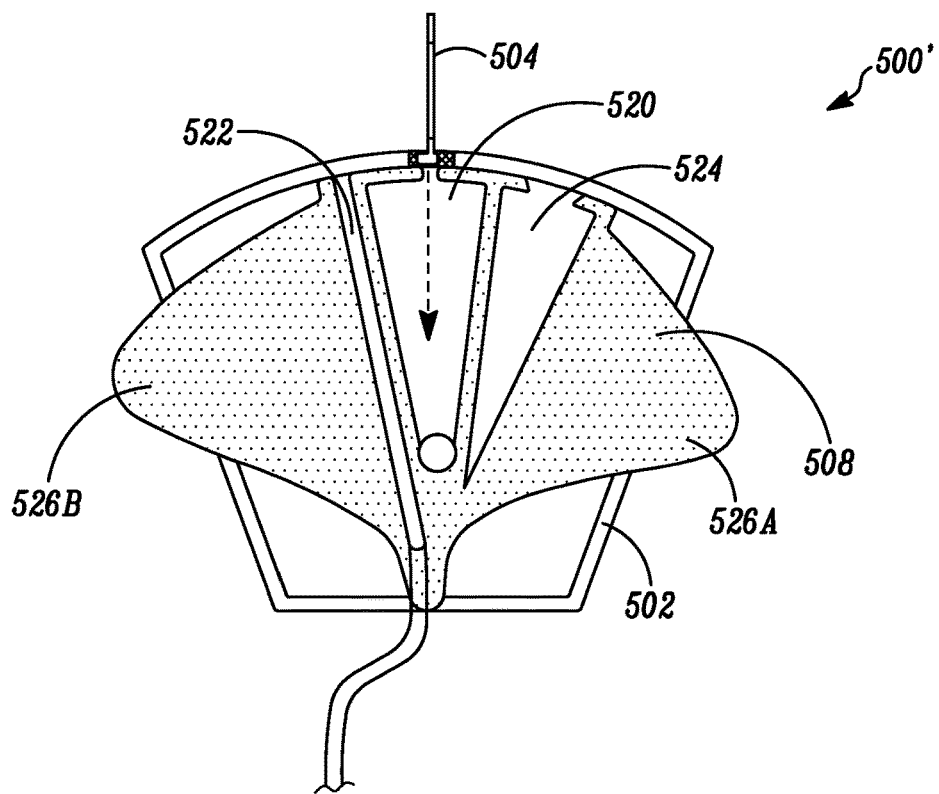
FIGS. 7A-D are plan views depicting an alternate movable element having a pair of push tabs in accordance with the fifth embodiment of the disclosure.
Figure 7B:
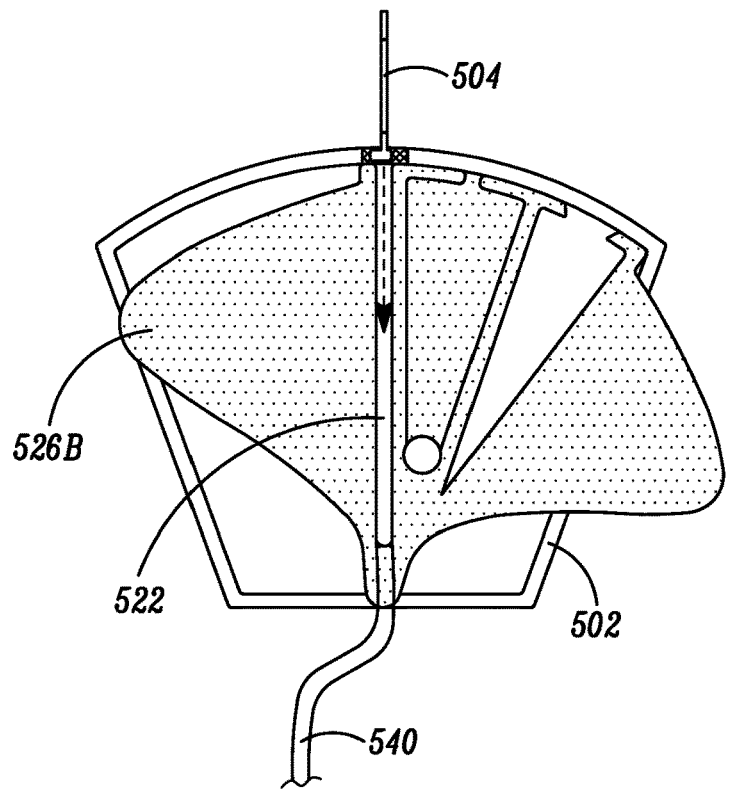
Figure 7C:
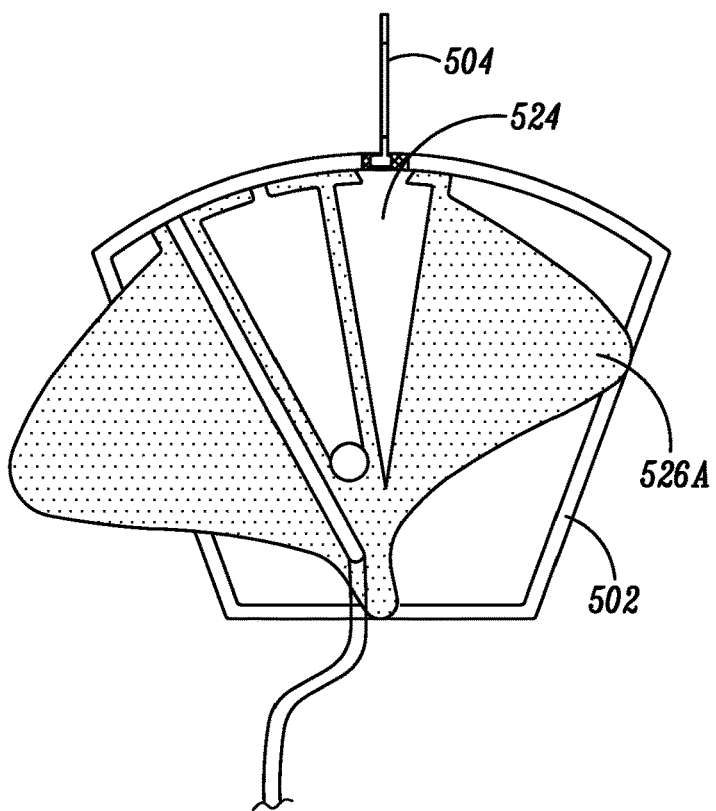
Figure 7D:
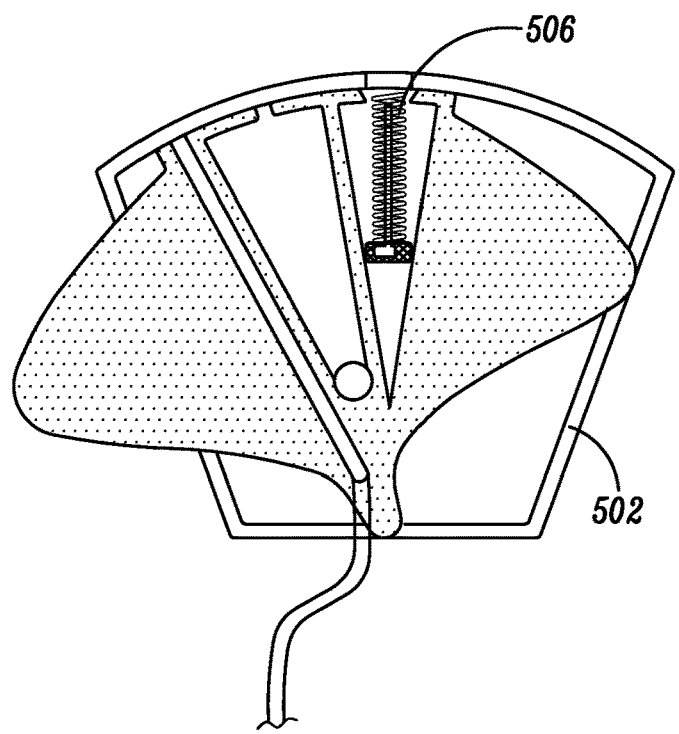

In embodiments, the shift between the initial sequestration position (as depicted in FIG. 7A) and the blood collection position (as depicted in FIG. 7B), and the shift from the blood collection position (as depicted in FIG. 7B) to the needle retraction position (as depicted in FIGS. 7C-D) can occur separately as fluid motions. In alternative embodiments, an interference protrusion may be introduced within the distal end, and within the rotation path of the movable element 508, such that the clinician is aware, via tactile feedback, that the movable element 508 is in the blood collection position and a pause is warranted. In yet other embodiments, a ratchet mechanism can be introduced into the pivoting point such that the movable element 508 ceases movement in the blood collection position and the clinician must manipulate the one or more push tabs 526A again to move the movable element 508 from the blood collection position to the needle retraction position, but bypassing the initial sequestration position.

In some embodiments, the blood sequestration device can further include a catheter assembly to aid in the collection of a blood sample. Referring to FIGS. 8A-D, a blood sequestration device 600 is depicted in accordance with a sixth embodiment of the disclosure. The blood sequestration device 600 can be configured to automatically retract and safely house a sharpened distal tip of a needle following the insertion of a catheter assembly for the collection of a blood sample. The blood sequestration device 600 can include a housing 602, needle 604, needle biasing mechanism 606, movable element 608, and catheter assembly 650.

Figure 8A:
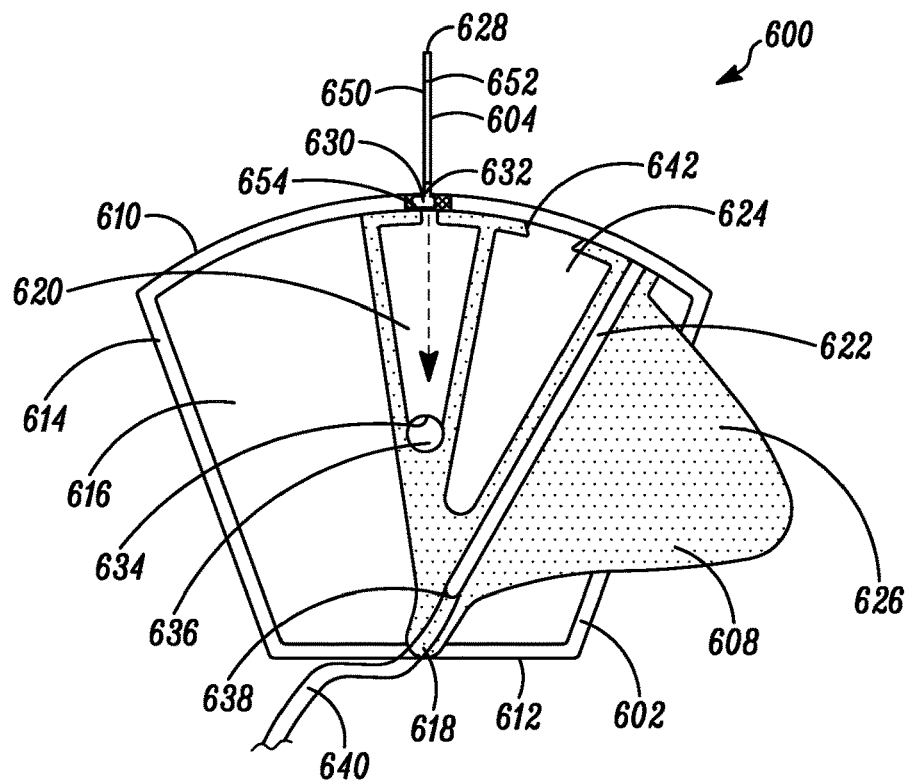
FIG. 8A-D are plan views depicting a blood sequestration device in accordance with a sixth embodiment of the disclosure.

The housing 602 can have a distal end 610, a proximal end 612 and a housing wall 614 defining a cavity 616. As depicted in FIG. 8A, in one embodiment, the housing 602 can generally be formed in the shape of a truncated sector, wherein the interior surface of the housing wall 614 along the distal end 610 forms an arc in which points along the interior surface of the housing wall 614 along the distal end 610 are generally equidistant from a point 618 located in proximity to the proximal end 612 of the housing 602.

Figure 8B:
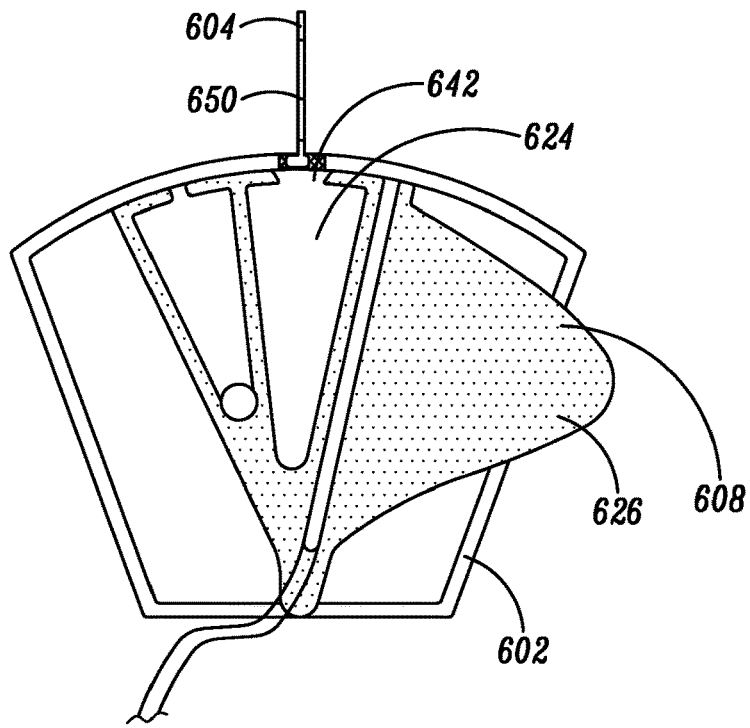
Figure 8C:
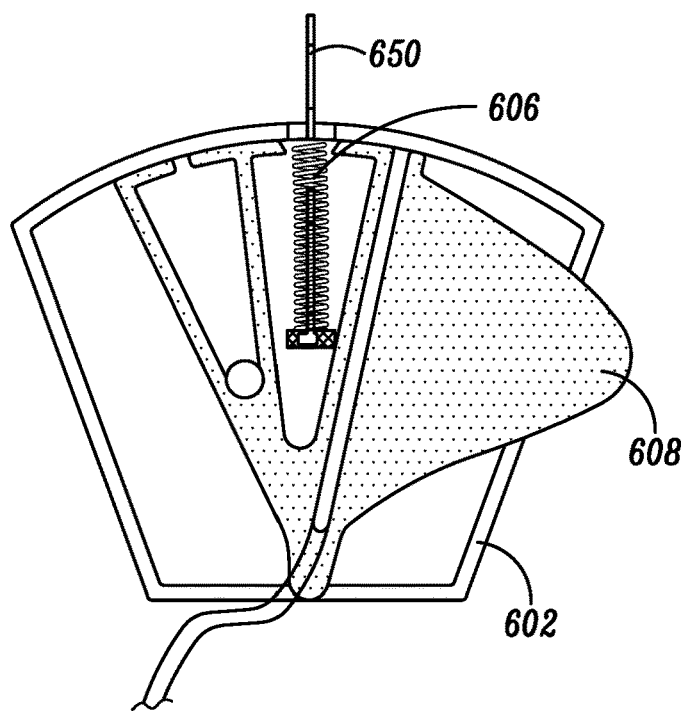
Figure 8D:
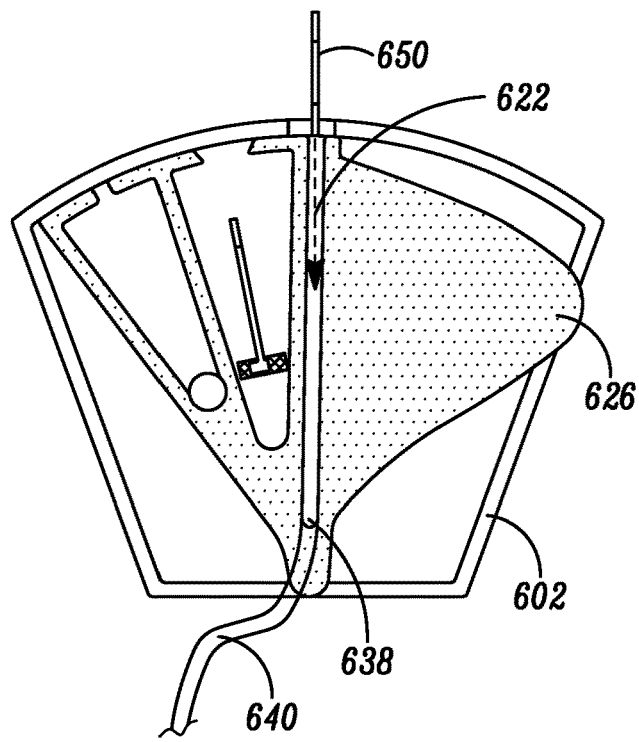

The movable element 608 can reside at least partially within the cavity 616 of the housing 602, and can be pivotably coupled to the housing 602 about a point 618, such that the movable element 608 is configured to rotate or shift relative to the housing 602 between an initial blood sequestration position (as depicted in FIG. 8A), a needle retraction position (as depicted in FIGS. 8B-C), and a blood collection position (as depicted in FIG. 8D).

In one embodiment, the movable element 608 can define one or more chambers and/or fluid pathways. For example, in one embodiment, the movable element 608 can define a sequestration chamber 620, a blood collection pathway 622, and a chamber 624 configured to house at least a portion of the needle 604 upon retraction. In one embodiment, the movable element 608 can further define one or more push tabs 626 configured to protrude from the housing 602 to enable a clinician to manipulate the movable element 608 relative to the housing 602 between the initial blood sequestration position, needle retraction position, and blood collection position.

The needle 604 can include an elongate cylindrical shaped metal structure defining a lumen that extends between a sharpened distal tip 628 and a proximal end 630. The sharpened distal tip 628 can be constructed and arranged to pierce the skin of the subject during needle insertion. The proximal end 630 of the needle 604 can be operably coupled to a needle hub 632. In some embodiments, the needle 604 and needle hub 632 can be collectively referred to as a needle assembly.

The needle hub 632 can be slidably coupled to the housing 602 between an initial position (as depicted in FIG. 8A), in which a least a portion of the needle 604 extends beyond the housing 602, and a safe position (as depicted in FIG. 8C), in which the sharpened distal tip 628 of the needle 604 is housed within the housing 602. The biasing mechanism 606 can be operably coupled between the needle hub 632 and the distal end of the housing 602, and can be configured to naturally bias the needle hub 632 to the safe position.

The catheter assembly 650 can include a catheter tube 652 and a catheter hub 654. The catheter assembly 650 can be configured to coaxially ride over at least a portion of the needle 604 and/or needle assembly. In one embodiment, the catheter hub 654 can be operably coupled to the distal end 610 of the housing 602.

In one embodiment, the blood sequestration device 600 can be provided in the initial blood sequestration position, with the needle 604 and catheter assembly 650 extending outwardly from the distal end 610 of the housing 602. Upon insertion of the needle 604 and catheter tube 652 into the vein of the subject, blood flows through the lumen of the needle 604, and into the sequestration chamber 620 defined within the movable element 608.

The sequestration chamber 620 can include a vent path 634 configured to enable the escape of gas initially trapped within the sequestration chamber 620, while inhibiting the escape of blood. For example, in one embodiment, the vent path 634 can be sealed by a plug 636, constructed of an air permeable, hydrophilic material that enables the passage of air, but inhibits the passage of liquid. Air that resides within the sequestration chamber 620 is therefore pushed through the plug 636 by the incoming blood, until the blood reaches the plug 636 or is otherwise stopped. In one embodiment, the sequestration chamber 620 has a volume of at least 0.15 mL, although other volumes of the sequestration chamber 620 are also contemplated.

Once an initial quantity of blood has been sequestered within the sequestration chamber 620, a clinician can manipulate the one or more push tabs 626 to cause the movable element 608 to shift from the initial blood sequestration position to the needle retraction position. Prior to movement of the movable element 608 to the needle retraction position, a distal surface of the movable element 608 can inhibit retraction of the needle 604 into the cavity 616 of the housing 602. By contrast, the chamber 624, configured to house at least a portion of the needle 604 upon retraction, can include structure defining an opening 642 shaped and sized to enable the needle hub 632 to pass therethrough, thereby enabling the needle 604 to be retracted within the chamber 624 under the natural bias of the needle biasing mechanism 606 to the safe position. In the safe position, the sharpened distal tip 628 of the needle 604 is housed within the chamber 624 to reduce the risk of unintended needle sticks, while leaving the catheter assembly 650 in place within the subject's vein.

Once the needle 604 has been safely retracted, a clinician can manipulate the one or more push tabs 626 to cause the movable element 608 to shift from the needle retraction position to the blood collection position. In the blood collection position, blood can flow from the vein of the subject through the catheter assembly 650, through the blood collection pathway 622 defined within the movable element 608, and out of the housing 602 through an outlet port 638, which can be operably coupled to a blood collection device via an extension tube 640. Once a satisfactory quantity of blood has been collected, a clinician can remove the catheter assembly 650 from the patient's vein.

In embodiments, the shift between the initial sequestration position (as depicted in FIG. 8A) and the needle retraction position (as depicted in FIGS. 8B-C), and the shift from the needle retraction position (as depicted in FIGS. 8B-C) and the blood collection position (as depicted in FIG. 8D) can occur as one fluid motion. In other words, after the initial blood flow is sequestered in the initial sequestration position, the clinician can manipulate the one or more push tabs 626 such that the movable element 608 rotates to the blood collection position, thereby rotating through the needle retraction position. In alternative embodiments, an interference protrusion may be introduced within the distal end, and within the rotation path of the movable element 608, such that the clinician is aware, via tactile feedback, that the movable element 608 is in the needle retraction position and a pause is warranted. In yet other embodiments, a ratchet mechanism can be introduced into pivoting point 618 such that the movable element 608 ceases movement in the needle retraction position and the clinician must manipulate the one or more push tabs 626 again to move the movable element from the needle retraction position to the blood collection position.

Figure 9C:
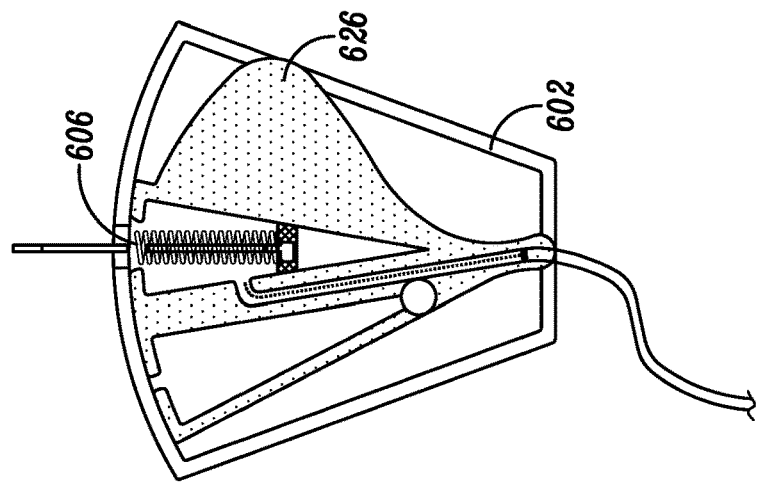
FIGS. 9A-C are plan views depicting an alternate movable element in which the needle retention chamber and blood collection pathway are combined in accordance with the sixth embodiment of the disclosure.
Figure 9B:
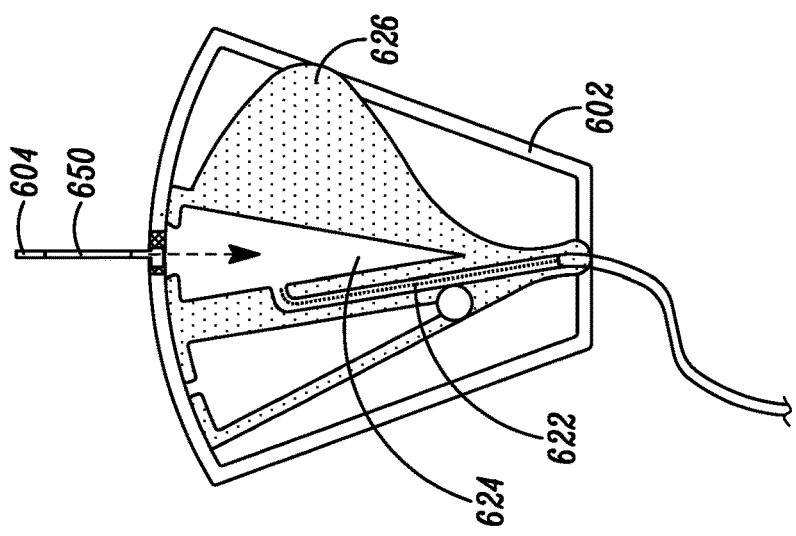
Figure 9A:
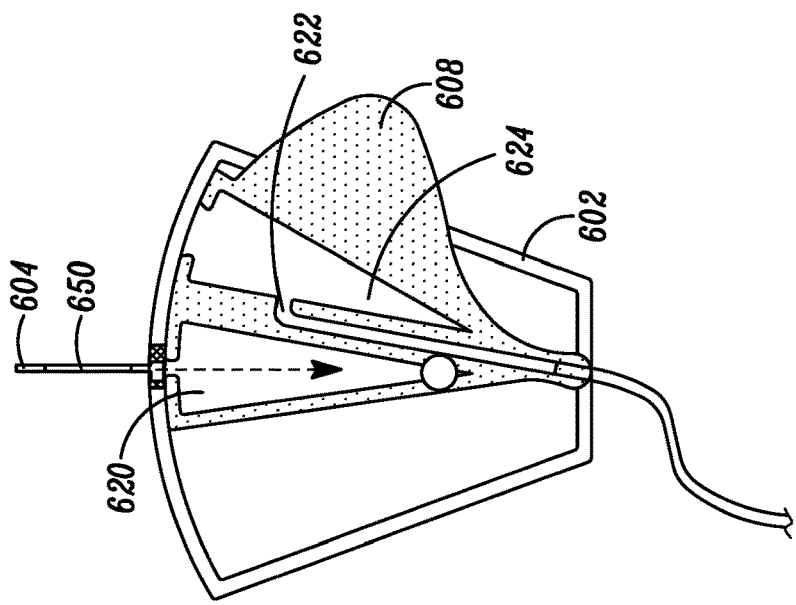

Referring to FIGS. 9A-C, in some embodiments, the blood collection pathway 622 and chamber 624 defined within the movable element 608 can be combined. In this embodiment, once an initial quantity of blood has been sequestered within the sequestration chamber 620, a clinician can manipulate the one or more push tabs 626 to move the movable element 608 to shift from the initial blood sequestration position to the blood collection position, which enables both retraction of the needle 604 within the chamber 624 under the natural bias of the needle biasing mechanism 606 to the safe position, as well as a flow of blood from the vein of the subject through the catheter assembly 650, through the blood collection pathway 622 defined within the movable element 608, and out of the housing 602 through an outlet port 638, which can be operably coupled to a blood collection device. Other configurations of chambers and/or fluid pathways within the movable element 608 are also contemplated.

In embodiments, the shift between the initial sequestration position (as depicted in FIG. 9A) and the blood collection and needle retraction position (as depicted in FIG. 9B-C), can occur freely. In alternative embodiments, an interference protrusion may be introduced within the distal end, and within the rotation path of the movable element 608, such that the moveable element 608 does not easily rotate into the blood collection and needle retraction position, unless the clinician purposefully manipulates the movable element 608 past the tactile feed back of the interference protrusion. In yet other embodiments, a ratchet mechanism can be introduced into the pivoting point such that the movable element 608 ceases movement in the initial sequestration position such that the clinician must manipulate the one or more push tabs 626 through the ratchet mechanism in order to move the movable element 608 from the interference protrusion to the blood collection position and needle retraction position.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. Reference in the specification to "one embodiment," "an embodiment," or "some embodiments" means that a particular feature, structure, or characteristic, described in connection with the embodiment, is included in at least one embodiment of the teaching. Appearances of the phrase "in one embodiment" in various places in the specification are not necessarily all referring to the same embodiment. Moreover, the embodiments described herein are not meant to be an exhaustive presentation of the ways in which the various features of the subject matter hereof may be combined, nor are the embodiments mutually exclusive combinations of features. Rather, the various embodiments can comprise a combination of different individual features selected from different individual embodiments, such that, as understood by persons of ordinary skill in the art, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A blood sequestration device configured to automatically retract and safely house a sharpened distal tip of a needle following the isolation of an initial portion of blood and collection of a subsequent sample of blood from a flow of blood of a patient, the blood sequestration device comprising:
   a needle having a sharpened distal tip;
   a sequestration body configured to coaxially ride over at least a portion of the needle in an initial blood collection position, the sequestration body having a vented sequestration chamber configured to isolate an initial portion of blood from a flow of blood while enabling escape of gas trapped within the sequestration chamber, the vented sequestration chamber defining a vent path sealed by a septum configured to enable at least a portion of the needle to pass therethrough while in the initial blood collection position, and an outlet port configured to be fluidly coupled to a blood collection device for the collection of a subsequent sample of blood from the flow of blood;
   a needle housing configured to selectively house the sharpened distal tip of the needle in a safe position; and
   a spring biasing mechanism positioned between the sequestration body and the needle housing and configured to bias the needle from the initial, blood collection position to the safe position, in which the sharpened distal tip of the needle is housed within the needle housing.

2. The blood sequestration device of claim 1, wherein the sequestration body includes one or more wings.

3. The blood sequestration device of claim 1, wherein the sequestration body includes a guide lock and the needle housing defines a channel in which the guide lock is configured to traverse.

4. The blood sequestration device of claim 3, wherein the guide lock is configured to selectively lock the sequestration body relative to the needle housing against a bias of the spring biasing mechanism in the blood collection position.

5. The blood sequestration device of claim 4, wherein rotation of the sequestration body relative to the needle housing enables automatic withdrawal of the sharpened distal tip of the needle into the needle housing.

* * * * *